United States Patent
Gombrich et al.

(10) Patent No.: US 11,957,322 B2
(45) Date of Patent: Apr. 16, 2024

(54) PERSONAL CERVICAL CELL COLLECTION DEVICE, KIT AND METHOD

(71) Applicant: OncoGenesis, Inc., Salt Lake City, UT (US)

(72) Inventors: Peter P. Gombrich, Salinas, CA (US); Christopher E. Todd, Campbell, CA (US)

(73) Assignee: OncoGenesis, Inc., Morgan Hill, CA (US)

( * ) Notice: Subject to any disclaimer, the term of this patent is extended or adjusted under 35 U.S.C. 154(b) by 0 days.

(21) Appl. No.: 17/670,173

(22) Filed: Feb. 11, 2022

(65) Prior Publication Data

US 2022/0160340 A1 May 26, 2022

Related U.S. Application Data

(63) Continuation of application No. 15/456,259, filed on Mar. 10, 2017, now Pat. No. 11,246,577.

(60) Provisional application No. 62/307,341, filed on Mar. 11, 2016.

(51) Int. Cl.
*A61B 10/02* (2006.01)

(52) U.S. Cl.
CPC .................. *A61B 10/0291* (2013.01)

(58) Field of Classification Search
None
See application file for complete search history.

(56) References Cited

U.S. PATENT DOCUMENTS

| | | | |
|---|---|---|---|
| 2,391,343 A | 12/1945 | Popper | |
| 3,592,186 A | 7/1971 | Oster | |
| 3,776,219 A | 12/1973 | Brown | |
| 4,821,741 A | 4/1989 | Mohajer | |
| 6,126,616 A | 10/2000 | Sanyal | |
| 6,346,086 B1 * | 2/2002 | Maksem | A61B 10/0291 600/572 |
| 6,352,513 B1 | 3/2002 | Anderson et al. | |
| 2009/0012424 A1 * | 1/2009 | Huschmand Nia | A61B 10/0045 600/569 |
| 2012/0157878 A1 | 6/2012 | Mendez | |
| 2014/0005648 A1 | 1/2014 | Burnett et al. | |

* cited by examiner

*Primary Examiner* — Benjamin S Melhus
*Assistant Examiner* — Samuel C Kim
(74) *Attorney, Agent, or Firm* — Patterson + Sheridan, LLP

(57) ABSTRACT

A cervical cell collection device, kit and method for the collection of cervical cells is provided. In some embodiments, the cervical cell collection device comprises an outer guide assembly having a distal end section with an aperture there through; an inner assembly positioned within the outer guide assembly, the inner assembly having a distal end with a collapsible collection pad secured thereto by a flexible collection support, wherein the inner assembly is movable from a first position where the collection pad is folded inside distal end section of the outer guide assembly to a second position where the collection pad is pushed through the aperture in the distal end of the outer guide assembly where it expands to contact and collect cervical cells.

18 Claims, 4 Drawing Sheets

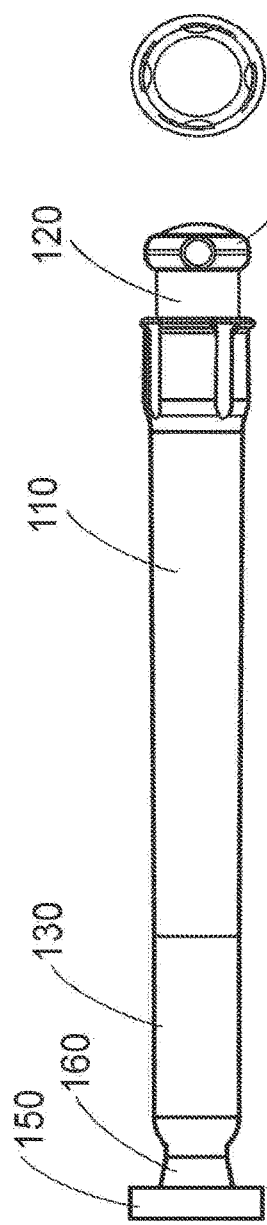
FIG. 2A
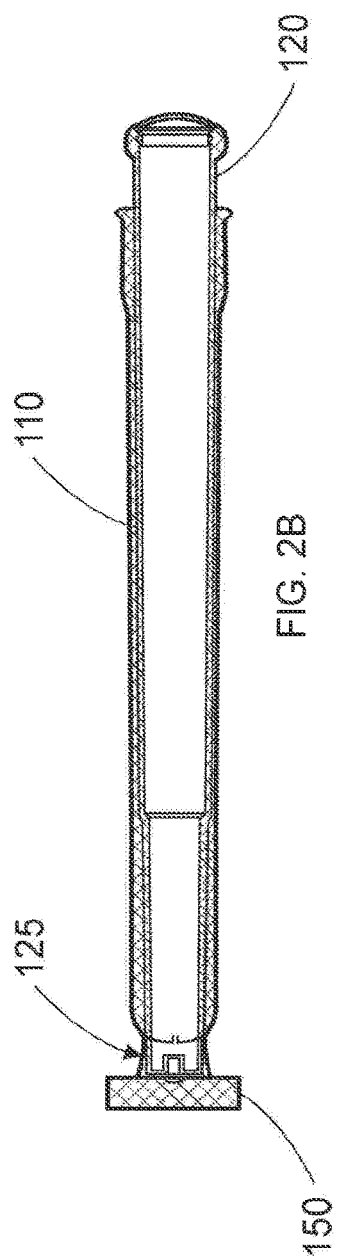
FIG. 2B
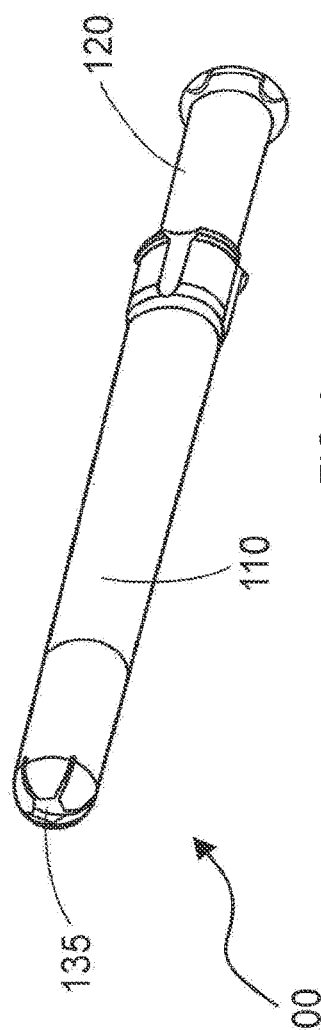
FIG. 3
FIGS. 2A-3

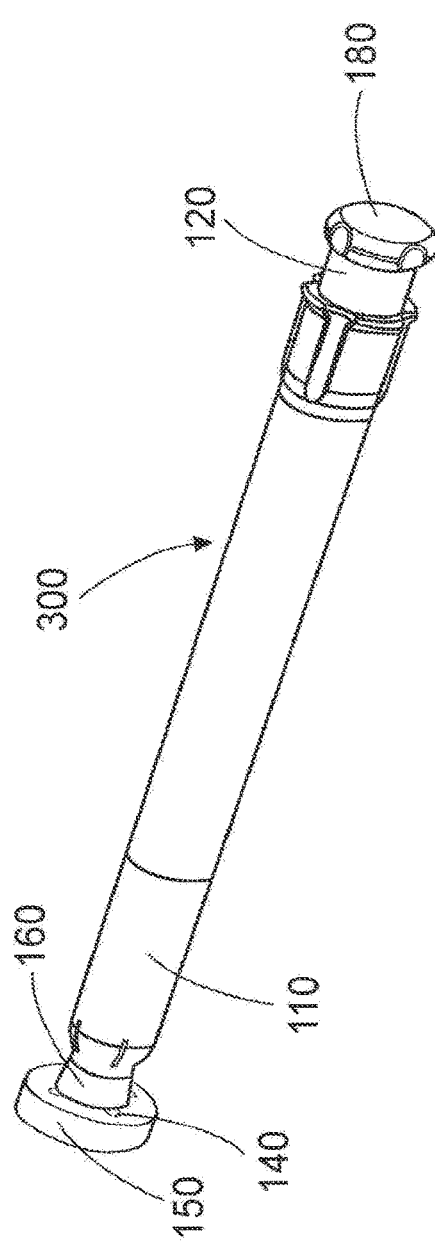
FIG. 4
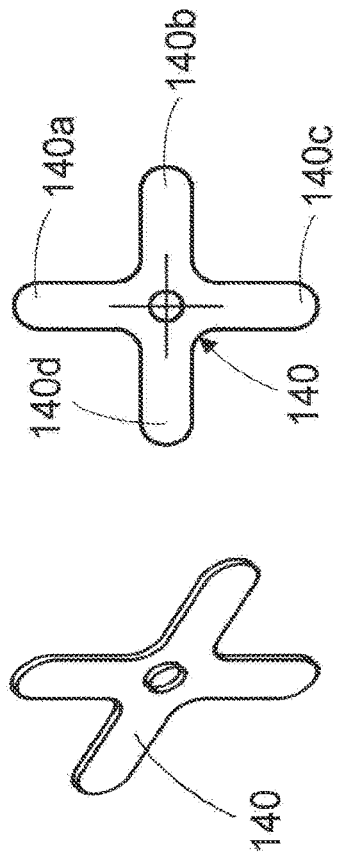
FIG. 6A
FIG. 6B
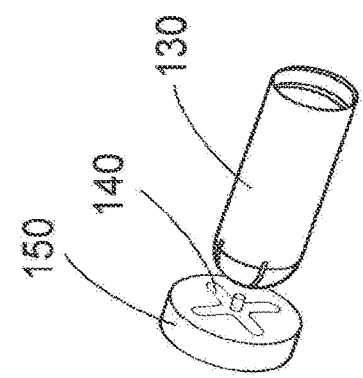
FIG. 5
FIGS. 4-6B

PERSONAL CERVICAL CELL COLLECTION DEVICE, KIT AND METHOD

CROSS-REFERENCE TO RELATED APPLICATIONS

This application is a continuation of co-pending U.S. patent application Ser. No. 15/456,259, filed Mar. 10, 2017, which claims benefit of U.S. Provisional Patent Application Ser. No. 62/307,341, filed Mar. 11, 2016. Each of the aforementioned related patent applications is herein incorporated by reference in its entirety.

BACKGROUND

Field

The present application relates generally to a cervical cell collection device, kit and method for the collection of cervical cells, and more specifically to a device, kit and method whereby cervical cell samples can be personally collected by a patient and then forwarded to a health care provider for analysis.

Description of the Related Art

According to a recent report from the World Health Organization, cervical cancer is the fifth most deadly cancer for women in the world. Cervical cancer screening is commonly based on cytological and colposcopic analyses. The generally accepted cytological smear of the cervix (Papanicolaou test or Pap smear) has led to a reduction in the incidences of and mortalities caused by cervical cancer.

Cervical cancer frequently begins as a precancerous lesion of the cervix. These lesions are also known as cervical intraepithelial neoplasia. If left untreated, these lesions can deepen over time and ultimately develop into an invasive cancer of the cervix and associated tissues. Fortunately, early detection followed by appropriate treatment results in a very high cure rate for cervical cancer.

Therefore, it is quite important that at least certain factions of the female population undergo regular screening. These factions include patients with previous cervical abnormalities and those who have a family history of cervical abnormalities. Women who are sexually active are at greater risk and should undergo regular screening, as are those who test positive for HPV (human papillomavirus).

The Pap screening test or Pap smear as commonly called, was developed by Dr. George Papanicolaou and detects cellular abnormalities and thus the development of potentially pre-cancerous lesions. Typically, the PAP test is performed in the physician's office as part of a woman's routine gynecological examination. The test involves collecting cervical cells via a brush, stick or swab that is used to loosen and then collect cells that can be examined microscopically.

In a Pap smear, the collected cells are placed on a glass slide and stained. In addition to a smear, in developed parts of the world the sample is placed into a preservative and then is sent to a lab for analysis, called Liquid Based Prep (LBP), and from there a slide is prepared using a machine or by spinning the sample with the cervical cells. The sample is examined by a specially-trained and qualified cytotechnologist using a light microscope. In short, it is a subjective analysis with several known disadvantages, such as an increase in false-negatives and equivocal results as a consequence of debris obscuring abnormal cells.

The PAP test is nearly always performed in a physician's office by a gynecologist or other medical professional. Thus, the test requires the expense of an office visit, and thus this means that the PAP test is not readily available to all women, for example, as would be desired in public health screening. Further, the test is considered by many women to be uncomfortable and embarrassing, and some women have religious beliefs that prohibit gynecological procedures such as the PAP test.

Thus a need remains for an apparatus that will extend cervical screening to more women by permitting women to easily and comfortably obtain a cervical cell sample without requiring a physician's assistance. Such an apparatus could be used, for example, to augment traditional PAP tests by providing cervical cell screening to women who would otherwise not have a PAP test. A personal cervical cell collection could also be used to confirm a previous diagnosis. While various designs have been developed, all suffer numerous limitations and no currently available personal collection has achieved meaningful adoption.

For example, for a personal collection device to be useful and accepted by the healthcare industry and patients, the device must be easy to use while obtaining a proper sample, meaning that the device needs to obtain cervical cells and without contamination from other cells. Thus, further developments and improvements are needed.

SUMMARY

A cervical cell collection device, kit and method for the collection of cervical cells is provided. More specifically to a device, kit and method whereby cervical cell samples can be personally collected by a patient and then forwarded to a health care provider for analysis is provided. Of particular advantage, the cervical cell collection device is designed for use by women who are not able to have a sample taken by a professional or who have elected to control their own cervical collection under their own controlled environment.

In some embodiments, a cervical cell collection device is provided, comprising: an outer guide assembly having a distal end section with an aperture there through; an inner assembly positioned within the outer guide assembly, the inner assembly having a distal end with a collapsible collection pad secured thereto by a flexible collection support, wherein the inner assembly is movable from a first position where the collection pad is folded inside distal end section of the outer guide assembly to a second position where the collection pad is pushed through the aperture in the distal end of the outer guide assembly where it expands to contact and collect cervical cells.

In other embodiments, a kit is provided comprising the cervical cell collection device described above and a container for receiving the collection pad with cervical cells thereon, and instructions for use of the device.

In other embodiments, a method of obtaining cervical cells without the assistance of healthcare personnel is provided, comprising the steps of: inserting a cervical cell collection device into the vagina of a patient, the cervical collection device being in a retracted position; once positioned next to the cervix, engaging the cervical collection device to an extended position such that a collection pad is exposed and contacts the cervix collecting the desired cervical cells, while inserted in the vagina, retracting the cervical collection device into a retracted position such that the collection pad is withdrawn within the collection device, and removing the cervical collection device from the vagina.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

FIGS. 2A and 2B are cross sectional views of the exemplary cervical cell collection device of FIG. 1;

FIG. 3 illustrates a perspective view of an exemplary cervical cell collection device in a retracted position;

FIG. 4 illustrates a perspective view of an exemplary cervical cell collection device in an extended position;

FIG. 5 illustrates a partial perspective view of the tip region of an exemplary cervical cell collection device;

FIGS. 6A and 6B illustrate perspective and front views, respectively, of the collection support member according to some embodiments;

DETAILED DESCRIPTION

Figure 1:
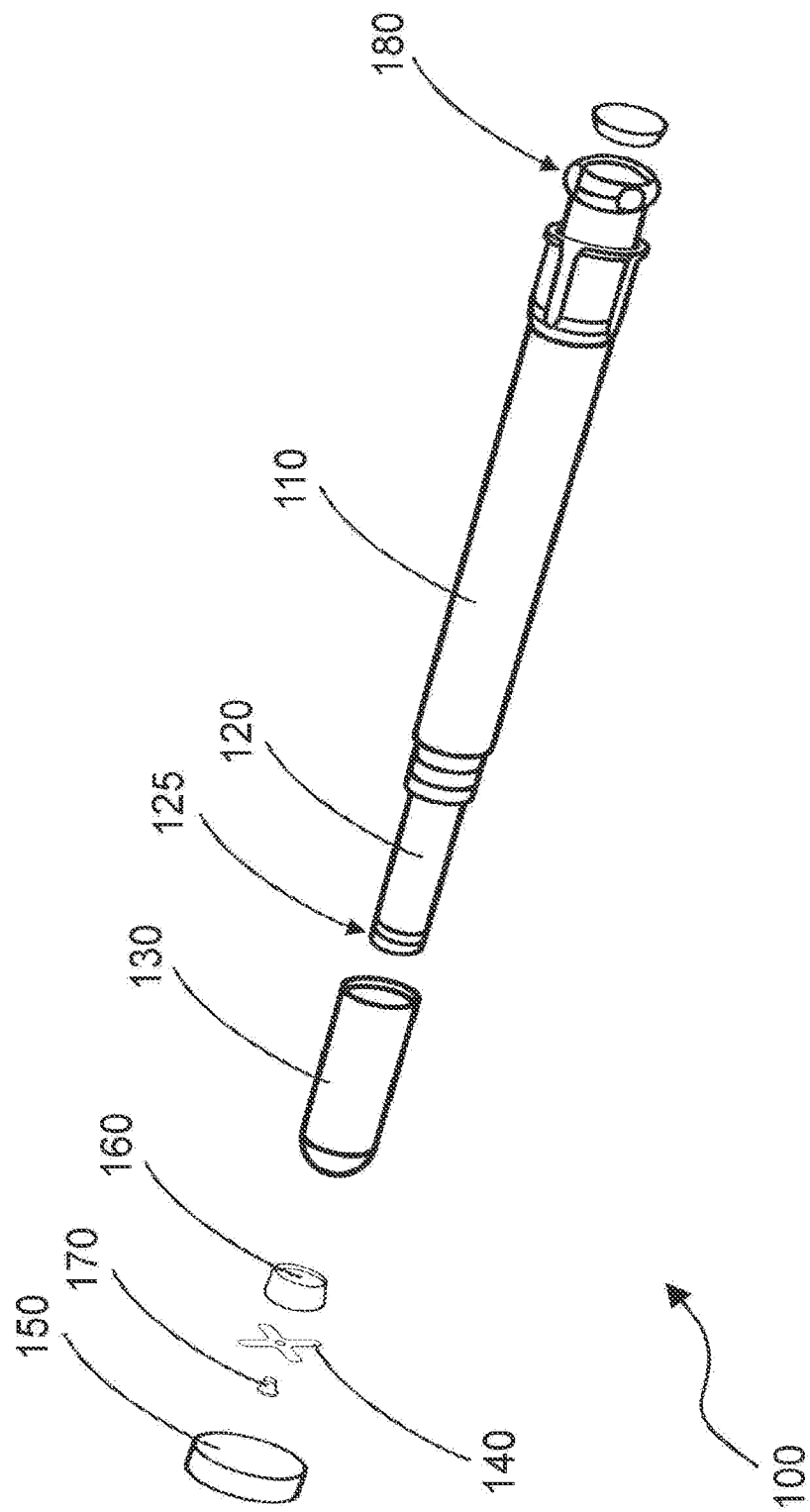
FIG. 1 illustrates an exploded view of an exemplary cervical cell collection device, according to some embodiments.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

A cervical cell collection device, kit and method for the collection of cervical cells is provided. More specifically to a device, kit and method whereby cervical cell samples can be personally collected by a patient and then forwarded to a health care provider for analysis is provided. The cervical cell collection device, kit and method provides a number of advantages, including but not limited to a device that provides a more consistent and controlled means for collecting cervical cells versus vaginal cells. The inventive device protects the collected sample from coming in contact with vaginal material such as blood, mucus and vaginal cells when the device is removed from the vaginal canal. The inventive device provides a means for a women to know when the device is in contact with the cervix as a rotating control handle provides feedback to her when she is in contact with the cervix and allows the outer guide assembly (described in detail below) to slide back when the collection pad or sponge comes into contact with the cervix.

Various embodiments are described below relating to a cervical cell collection device, comprising: an outer guide assembly having a distal end section with an aperture there through; an inner assembly positioned within the outer guide assembly, the inner assembly having a distal end with a collapsible collection pad secured thereto by a flexible collection support, wherein the inner assembly is movable from a first position where the collection pad is folded inside distal end section of the outer guide assembly to a second position where the collection pad is pushed through the aperture in the distal end of the outer guide assembly where it expands to contact and collect cervical cells.

Various embodiments are described below relating to a kit comprising the cervical cell collection device described above and a container for receiving the collection pad with cervical cells thereon, and instructions for use of the device.

Various embodiments are described below relating to a method of obtaining cervical cells without the assistance of healthcare personnel, comprising the steps of: inserting a cervical cell collection device into the vagina of a patient, the cervical collection device being in a retracted position; once positioned next to the cervix, engaging the cervical collection device to an extended position such that a collection pad is exposed and contacts the cervix, while inserted in the vagina collecting the desired cervical cells, retracting the cervical collection device into a retracted position such that the collection pad is withdrawn within the collection device, and removing the cervical collection device from the vagina.

Embodiments of the present invention provide a number of advantages. For example, the collection pad is protected during insertion and removal from and into the vagina canal such that contamination with cells and tissue does not occur. The collection pad auto expands to collect cervical cells only, and thus does not collect vaginal cells. Thus, contamination of the sample is reduced and/or eliminated.

FIG. 1 illustrates an exploded view of an exemplary cervical cell collection device 100 according to one embodiment of the present invention. For purposes of explanation, cervical collection device 100 will be discussed with respect to the collection of cervical cells from a cervix for Pap screening, however it will be appreciated that cervical collection device 100 may be used for other cell collection purposes.

Referring again to FIG. 1, and the cross sectional views shown in FIGS. 2A and 2B, cervical cell collection device 100 is comprised generally of an outer guide assembly 110 having a distal end section 130 with an aperture 135 there through. An inner guide assembly 120 is slidably received and positioned within the outer guide assembly 110. The inner guide assembly 120 has a collapsible collection pad or sponge 150 at the distal end 125 and a grippable control handle 180 at the proximal end. The collection pad 150 is secured to the inner guide assembly 120 by flexible collection support 140, tip mount 160 and press fitting pin 170. Control handle 180 is used to slide and manipulate the inner assembly 120 within the outer assembly when operated, and to provide feedback to the women when she is in contact with the cervix, as described in more detail below. The outer and inner guide assemblies 110, 120 are substantially circular in cross-section.

The inner assembly 120 is movable from a first position where collection pad 150 is folded inside the distal end section 130 of the outer guide assembly 110, to a second position where the collection pad 150 is pushed through the aperture 135 in the distal end section 130 of the outer guide assembly 110 and expands to contact the cervix of the patient and collect cervical cells.

FIGS. 3 and 4 illustrate concepts of an exemplary use of the cervical cell collection device 100 in accordance with embodiments of the present application. In one example illustrated by FIG. 3, the cervical cell collection device 100 is in a first, or retracted, position. FIG. 4 illustrates the cervical cell collection device 100 in a second, or extended, position. More specifically, when the cervical cell collection device 100 is in the retracted position, inner guide assembly 120 is in a retracted position with respect the to the outer guide assembly 110, as depicted in FIG. 3. In this retracted position, the collection pad 150 is fully enclosed within the distal end portion 130 of the outer guide assembly 110. In this state, collection pad 150 is folded, or collapsed, within the outer guide assembly. This arrangement protects and isolates collection pad 150 during insertion and removal of the device 100 in and from the vaginal canal.

Once the cervical cell collection device is positioned adjacent the cervix, the control handle 180 on the inner guide assembly 120 is pushed forward to push collection pad 150 through the aperture 135 in the distal end section 130 of the outer guide assembly 110; thus moving to the expanded, or second, position as shown in FIGS. 4 and 5. As the collection pad 150 emerges from the aperture 135, it expands, or unfolds, to its full shape as shown in FIGS. 4 and 5. In this expanded state, collection pad 150 contacts the cervix of the patient. The outer guide assembly 110 slides back when the collection pad or sponge 150 comes into contact with the cervix, and this signals to the women that the collection pad is in contact with the cervix. The control handle 180 is configured to be rotated by the women, thereby rotating the collection pad 150 and collecting cervical cells onto the collection pad. Once the cervical cells are collected, the handle 180 is pulled back, causing the collection pad to fold, or collapse back down, as it is drawn back through the aperture 135 and into the outer guide assembly.

Collection pad 150 may be comprised of shape suitable for the collection of cervical cells from the cervix. Preferably, but not necessarily, collection pad 150 is disk shaped, circular or cylindrical shaped. In some embodiment, collection pad 150 is configured to pivot, in addition to rotating, in order to adjust to the surface plane of the cervix, thus providing a better opportunity to collect a sample from the complete ectocervical area. Collection pad 150 is comprised of any biocompatible material suitable for the collection of cervical cells from the cervix. Preferably, but not necessarily, collection pad 150 may be comprised of an open-celled porous material such as foam, sponge or the like. In some embodiments the collection pad 150 may be coated with a suitable material to enhance exfoliation or adherence of the cervical cells to the pad. Preferably, collection pad 150 has texture and porosity sufficient to capture cervical cells, yet allow the release of substantially all of the cervical cells collected.

Of particular advantage, collection pad 150 is comprised of a pliable material and configured such that the pad can fold into a collapsed or folded shape when housed within the outer guide assembly 110 and then expand to its full open shape when extended (as shown in FIG. 5 in particular, with tip mount 160 removed from the view for clarity). To achieve this feature and operability, collection support 140 is employed. Collection support 140 is affixed to the back side of collection pad 150, meaning the surface of the collection pad that does not contact the cervix. Collection support 140 is comprised of a material that exhibits sufficient rigidity, yet is flexible, and which manipulates the shape of collection pad 150 as the inner guide assembly 120 is moved between the retracted and extended positions. In some embodiments, collection support 140 is comprised of plastic. Collection support 140 is affixed to the distal end of inner guide assembly 120 by tip mount 160 and press fitting pin 170.

An exemplary embodiment of collection support 140 is shown in further detail with reference to FIGS. 6A and 6B. Collection support 140 may be formed of any shape suitable for folding collection pad 150 into the outer guide assembly 110 and then expanding collection pad 150 into its full expanded shape and maintaining this expanded state during collection of the cervical cells. In one preferred embodiment, collection support 140 is comprised of a cross like shape, having four equal-distance arm members 140a, 140b, 140c, 140d spaced at 90 degrees as illustrated in FIGS. 6A and 6B. Alternatively, collection support 140 may be comprised of a triangular shape with three equal-distance members spaced at 120 degrees. As will be appreciated by those of ordinary skill in the art, any number of members may be used, including as little as two members. Collection support 140 may be affixed to the collection pad 150 by an adhesive. Any suitable biocompatible adhesive may be used that exhibits suitable bond strength.

Figure 7A:
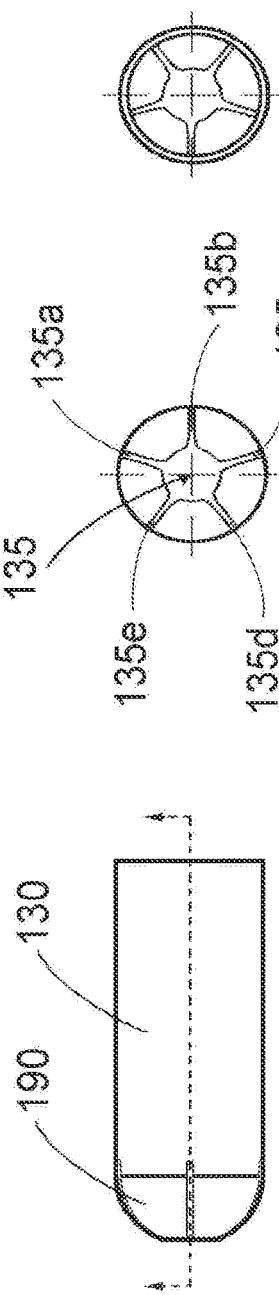
FIGS. 7A and 7B illustrate side and front views, respectively of the tip region of an exemplary cervical cell collection device.
Figure 7:
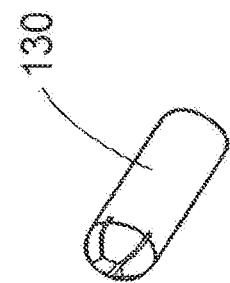
Figure 8:
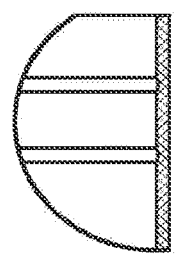
FIGS. 8A, 8B and 8C illustrate multiple views of tip region of an exemplary cervical cell collection device.
Figure 8C:
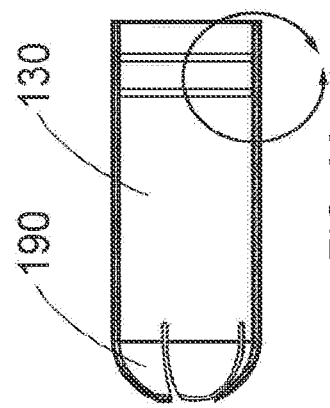

As described above, collection pad 150 is retracted into, and expanded out of, the distal end of outer guide assembly 130, which is illustrated in detail with reference to FIGS. 7 and 8. For comfort and safety during insertion and removal of the cervical cell collection device 100, distal end of outer guide assembly 130 has a rounded tip 190. The rounded tip 190 also acts to protect the collection pad 150 while in the retracted position by limiting or preventing exposure to vaginal cells, tissue and mucus during insertion and withdrawal from the vaginal canal. In some embodiments, aperture 135 may be formed of a single opening. Preferably, aperture 135 is formed of a center opening and a number of individual cut-out segments 135a, 135b, 135c, 136d, 135e as illustrated in FIG. 7B that open when the collection pad 150 is moved into the extended position. While five individual cut-out segments are shown in the exemplary embodiment, any suitable number may be used and the invention is not limited to the specific embodiments shown in the figures. The tip 190 is preferably comprised of a material, such as plastic, that exhibits sufficient flexibility to open when the collection pad 150 is moved into the extended position, but maintains its closed shape after the collection pad 150 is retracted back into the outer guide assembly 110.

A personal cervical cell collection kit is also disclose that includes the cervical cell collection device described above, fixative container, and instructions for use. More specifically, once the cervical cells are collected on the collection pad 150, the cells are placed in a liquid preservative. In some embodiments, the collection pad 150 is inserted into a liquid preservative in a container or vial and is swished to remove the collected cells. Once the cells are in the preservative, the container or vial is sent to a healthcare provider or lab for analysis in a controlled environment. The sample collected using the inventive cervical cell collection device may be analyzed for HPV/cytology or marker analysis, among other tests.

In another aspect, a method of obtaining cervical cells without the assistance of healthcare personnel is provided, In some embodiments, the method is carried out by inserting the cervical cell collection device 100 into the vagina of a patient, the cervical collection device being in a retracted position. The device is inserted until resistance is encountered, and thus is now adjacent the cervix. Once the device 100 is positioned next to the cervix, the cervical collection device 100 is moved to the extended position by pushing the grip or handle 180 on the inner guide assembly 120 toward the outer guide assembly 110, whereby the collection pad 150 is exposed and contacts the cervix. In some embodiments, the handle 180 may be rotated which rotates the collection pad 150 in order to provide more contact with the cervix to collect cervical cells. Next, while inserted in the vagina, the cervical collection device 100 is moved into a retracted position by pulling the handle 180 to drawn the collection pad 150 into the outer guide assembly 110. Once the collection pad 150 is folded back into the outer guide assembly 110, the cervical collection device 100 is withdrawn from the vagina.

While the invention has been described with reference to specific embodiments, it will be apparent to those skilled in the art that many alternatives, modifications and variations may be made. Accordingly, the present invention is intended to embrace all such alternatives, modifications and variations that may fall within the spirit and scope of the appended claims.

The invention claimed is:

1. A cell sample collection device, comprising:
an outer guide assembly, comprising:
a distal end with a rounded tip, the rounded tip having an aperture disposed therethrough, the aperture comprising a center opening and a plurality of cut-out segments; and
an inner guide assembly slidably received within the outer guide assembly, the inner guide assembly comprising:
a proximal end having a control handle; and
a distal end having a tip mount attached thereto, the tip mount having a frustoconical shape;
a collection support attached to the tip mount, the collection support comprising a plurality of arm members, each of the plurality of arm members fixedly coupled to a backside of a collection pad;
the collection pad secured to the collection support via a press fitting pin disposed through an opening in the collection support;
wherein the inner guide assembly is movable from a first position where the collection pad is collapsed inside the distal end of the outer guide assembly and isolated from an exterior of the outer guide assembly to prevent contamination of the collection pad during positioning of the cell sample collection device for collecting a cell sample from a cell sample surface, to a second position where the collection pad is pushed through the aperture in the rounded tip of the outer guide assembly and expands into a full shape of the collection pad to contact and collect the cell sample from the cell sample surface, and
wherein the outer guide assembly is configured to slide proximally along the inner guide assembly when the collection pad, in the second position, contacts the cell sample surface for providing feedback to a user indicating that the contact has been made.

2. The cell sample collection device of claim 1, wherein the collection pad is secured to the inner guide assembly such that rotation of the control handle causes rotation of the collection pad.

3. The cell sample collection device of claim 2, wherein the collection pad is configured to pivot to adjust to a surface plane of the cell sample surface.

4. The cell sample collection device of claim 1, wherein the full shape of the collection pad is disk-shaped, circular, or cylindrical-shaped.

5. The cell sample collection device of claim 4, wherein the collection support is planar when the collection pad is expanded to the full shape.

6. The cell sample collection device of claim 5, wherein the collection support comprises a triangular shape.

7. The cell sample collection device of claim 5, wherein the collection support comprises a cross shape.

8. The cell sample collection device of claim 1, wherein the collection pad is comprised of an open-celled and porous biocompatible material.

9. A cell sample collection device, comprising:
an outer guide assembly, comprising:
a distal end with an aperture disposed therethrough, the aperture comprising a center opening and a plurality of cut-out segments; and
an inner guide assembly slidably received within the outer guide assembly, the inner guide assembly comprising:
a distal end having a tip mount attached thereto, the tip mount having a frustoconical shape;
a collection support attached to the tip mount via a press fitting pin, the press fitting pin disposed through an opening in the collection support and extending from a first side of the collection support to a second side of the collection support, the collection support comprising a plurality of arm members, each of the plurality of arm members fixedly coupled to a backside of a collection pad;
the collection pad secured to the collection support;
wherein the inner guide assembly is movable from a first position where the collection pad is collapsed inside the distal end of the outer guide assembly, to a second position where the collection pad is pushed through the aperture in the outer guide assembly, and
wherein the outer guide assembly is configured to slide proximally along the inner guide assembly when the collection pad, in the second position, contacts a cell sample surface for providing feedback to a user indicating that the contact has been made.

10. The cell sample collection device of claim 9, wherein the collection pad is configured to expand into a full shape of the collection pad when in the second position to contact and collect a cell sample from the cell sample surface.

11. The cell sample collection device of claim 9, wherein the aperture is disposed through a rounded tip of the outer guide assembly, the rounded tip configured to protect the collection pad when in the first position.

12. The cell sample collection device of claim 9, wherein the collection pad is secured to the inner guide assembly such that rotation of the inner guide assembly causes rotation of the collection pad.

13. The cell sample collection device of claim 12, wherein the collection pad is configured to pivot to adjust to a surface plane of the cell sample surface.

14. A cell sample collection device, comprising:
an outer guide assembly, comprising:
a distal end with an aperture disposed therethrough; and
an inner guide assembly slidably received within the outer guide assembly, the inner guide assembly comprising:
a distal end having a tip mount attached thereto, the tip mount having a frustoconical shape, wherein a most distal portion of the tip mount has a larger diameter than a most proximal portion of the tip mount;
a collection support attached to the tip mount via a press fitting pin, the press fitting pin disposed through an opening in the collection support and extending from a first side of the collection support to a second side of the collection support, the collection support comprising a plurality of arm members, each of the plurality of arm members fixedly coupled to a backside of a collection pad;

the collection pad secured to the collection support;

wherein the inner guide assembly is movable from a first position where the collection pad is collapsed inside the distal end of the outer guide assembly, to a second position where the collection pad is pushed through the aperture in the outer guide assembly, and wherein the outer guide assembly is configured to slide proximally along the inner guide assembly when the collection pad, in the second position, contacts a cell sample surface for providing feedback to a user indicating that the contact has been made.

15. The cell sample collection device of claim 14, wherein the collection pad is configured to expand into a full shape of the collection pad when in the second position to contact and collect a cell sample from the cell sample surface.

16. The cell sample collection device of claim 14, wherein the aperture is disposed through a rounded tip of the outer guide assembly, the rounded tip configured to protect the collection pad when in the first position.

17. The cell sample collection device of claim 14, wherein the collection pad is secured to the inner guide assembly such that rotation of the inner guide assembly causes rotation of the collection pad.

18. The cell sample collection device of claim 17, wherein the collection pad is configured to pivot to adjust to a surface plane of the cell sample surface.

* * * * *